(12) United States Patent
Tedgui et al.

(10) Patent No.: US 9,193,971 B2
(45) Date of Patent: Nov. 24, 2015

(54) METHODS FOR THE TREATMENT OF NONALCOHOLIC STEATOHEPATITIS

(71) Applicants: INSERM (Institut National de la Sante et de la Recherche Medicale), Paris (FR); Universite Paris Descartes, Paris (FR)

(72) Inventors: Alain Tedgui, Paris (FR); Xavier Loyer, Paris (FR); Pierre-Emmanuel Rautou, Chapel Hill, NC (US)

(73) Assignees: Institut National de la Sante et de la Recherche Medicale (INSERM), Paris (FR); Universite Paris Descartes, Paris (FR)

( * ) Notice: Subject to any disclaimer, the term of this patent is extended or adjusted under 35 U.S.C. 154(b) by 0 days.

(21) Appl. No.: 14/390,918

(22) PCT Filed: Apr. 10, 2013

(86) PCT No.: PCT/EP2013/057437
§ 371 (c)(1),
(2) Date: Oct. 6, 2014

(87) PCT Pub. No.: WO2013/153082
PCT Pub. Date: Oct. 17, 2013

(65) Prior Publication Data
US 2015/0057332 A1    Feb. 26, 2015

(30) Foreign Application Priority Data

Apr. 10, 2012  (EP) .................................. 12305420

(51) Int. Cl.
| | |
|---|---|
| *A61K 48/00* | (2006.01) |
| *C07H 21/02* | (2006.01) |
| *C07H 21/04* | (2006.01) |
| *C12N 15/63* | (2006.01) |
| *C12N 15/113* | (2010.01) |
| *A61K 31/7105* | (2006.01) |
| *A61K 31/7125* | (2006.01) |
| *A61K 31/713* | (2006.01) |
| *C12N 7/00* | (2006.01) |

(52) U.S. Cl.
CPC ............ *C12N 15/113* (2013.01); *A61K 31/713* (2013.01); *A61K 31/7105* (2013.01); *A61K 31/7125* (2013.01); *C12N 7/00* (2013.01); *A61K 48/00* (2013.01); *C12N 2310/11* (2013.01); *C12N 2310/113* (2013.01); *C12N 2310/14* (2013.01); *C12N 2710/10042* (2013.01); *C12N 2710/16142* (2013.01); *C12N 2710/16442* (2013.01); *C12N 2740/15042* (2013.01)

(58) Field of Classification Search
CPC ..... A61K 48/00; C12N 15/111; C12N 15/113
See application file for complete search history.

(56) References Cited

U.S. PATENT DOCUMENTS

2010/0330155 A1* 12/2010 Berry et al. .................... 424/450

FOREIGN PATENT DOCUMENTS

WO    2009/106367    9/2009

OTHER PUBLICATIONS

Estep et al.; "Differential expression of miRNAs in the visceral adipose tissue of patients with non-alcoholic fatty liver disease"; Alimentary Pharmacology & Therapeutics, vol. 32, No. 3, Aug. 2010, pp. 487-497.
Cermelli et al.; "Circulating microRNAs in patients with chronic hepatitis C and non-alcoholic fatty liver disease"; PLoS One, vol. 6, No. 8, Aug. 2011, pp. 1-8.
Wang et al.; "Role of microRNA-155 at early stages of hepatocarcinogenesis induced by choline-deficient and amino acid-defined diet in C57BL/6 mice"; Hepatology, vol. 50, No. 4, Oct. 1, 2009, pp. 1152-1161.
Bahcecioglu et al.; "Lycopene prevents development of steatohepatitis in experimental nonalcoholic steatohepatitis model induced by high-fat diet"; Veterinary Medicine International, vol. 2010, Article ID 262179, 2010, the entire document (8 pages).
Wang et al.; "Dietary lycopene and tomato extract supplementations inhibit nonalcoholic steatohepatitis-promoted hepatocarcinogenesis in rats"; International Journal of Cancer, vol. 126, No. 8, Apr. 1, 2010, pp. 1788-1796.
Alisi et al.; "Mirnome analysis reveals novel molecular determinants in the pathogenesis of diet-induced nonalcoholic fatty liver disease"; Laboratory Investigation: A Journal of Technical Methods and Pathology, vol. 91, No. 2, Feb. 2011, pp. 283-293.

* cited by examiner

*Primary Examiner* — Amy Bowman
(74) *Attorney, Agent, or Firm* — Whitham Curtis Christofferson & Cook, PC

(57) ABSTRACT

The present invention relates to the treatment of nonalcoholic steatohepatitis (NASH), in particular to a compound that inhibits miR-21 expression for use in the treatment of nonalcoholic steatohepatitis.

5 Claims, 10 Drawing Sheets

```
                       SEQUENCE LISTING

<160> NUMBER OF SEQ ID NOS: 2

<210> SEQ ID NO 1
<211> LENGTH: 22
<212> TYPE: RNA
<213> ORGANISM: Artificial Sequence
<220> FEATURE:
<223> OTHER INFORMATION: Synthetic Antagomir-21

<400> SEQUENCE: 1
ucaacaucag ucugauaagc ua                                              22

<210> SEQ ID NO 2
<211> LENGTH: 22
<212> TYPE: RNA
<213> ORGANISM: Artificial Sequence
<220> FEATURE:
<223> OTHER INFORMATION: Synthetic Antagomir control

<400> SEQUENCE: 2
aaggcaagcu gacccugaag uu                                              22
```

METHODS FOR THE TREATMENT OF NONALCOHOLIC STEATOHEPATITIS

FIELD OF THE INVENTION

Figure 1:
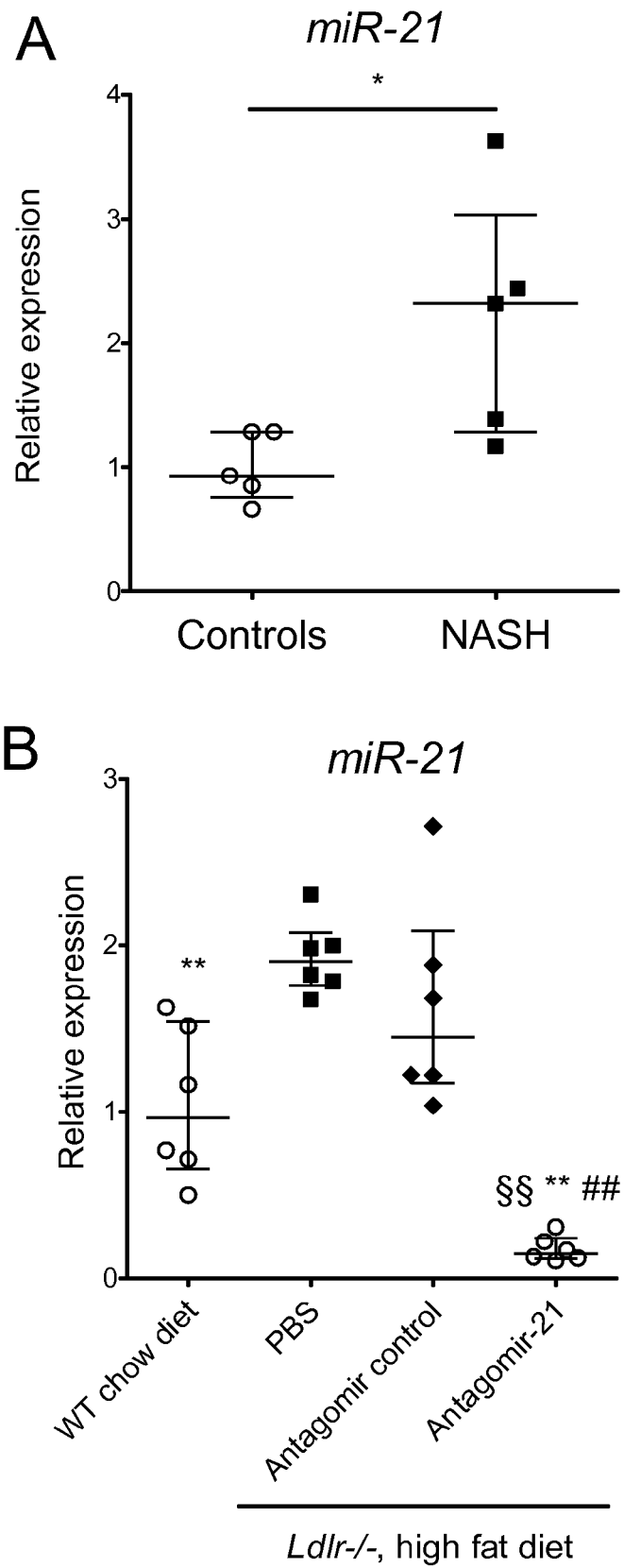

The present invention relates to the treatment of nonalcoholic steatohepatitis.

BACKGROUND OF THE INVENTION

Nonalcoholic fatty liver disease (NAFLD) and nonalcoholic steatohepatitis (NASH) are increasingly relevant public health issues owing to their close association with the worldwide epidemics of diabetes and obesity (Ratziu et al. (2010), J. Hepatol. 53(2):372-384). NAFLD and NASH are ones of the most common chronic liver diseases. Indeed, in a recent US survey, 39% of newly identified cases of chronic liver disease had NAFLD (Weston et al. (2005), Hepatology 41(2): 372-379). Chronic inflammation and fibrosis are key features of NASH, distinguishing it from the relatively benign NAFLD. NASH has potential for fibrosis, cirrhosis decompensation, and hepatocellular carcinoma. Despite its severity and prevalence, there are no approved treatments for NASH. Therefore, there is a need to develop new drugs that will be suitable for treatment of NASH. In this way, characterisation of new therapeutic targets in NASH is highly desirable.

MicroRNAs (miRNAs) are a family of noncoding RNAs, 19-22 nucleotides in length that regulate gene expression at the posttranscriptional level via messenger RNA (mRNA) degradation or translational inhibition (Bartel (2009), Cell 136(2):215-233).

There is no disclosure in the art of a functional role of miR-21 in NASH, nor a cause-effect relationship of miR-21 with NASH, nor the provision of a beneficial effect of the use of compounds that inhibits miR-21 expression in the treatment of NASH.

SUMMARY OF THE INVENTION

The present invention relates to a miR-21 inhibitor compound for use in the treatment of NASH in a patient in need thereof.

DETAILED DESCRIPTION OF THE INVENTION

The inventors aimed at investigating and identifying the role of miR-21 in NASH using an in vivo approach based on the miR-21 specific inhibitor antagomir-21.

The inventors first determined miR-21 expression in the liver of NASH patients as compared to controls with no or mild abnormalities. The inventors demonstrated that miR-21 was overexpressed in the liver of NASH patients. The inventors also assessed miR-21 expression in Ldlr$^{-/-}$ mice fed a high fat diet. This mouse model of NASH reproduced human features since miR-21 was upregulated in the liver in these mice. The inventors also demonstrated that miR-21 was primarily expressed in biliary and inflammatory cells in the liver of NASH patients and of Ldlr$^{-/-}$ mice under high fat diet. The inventors surprisingly found that treatment of Ldlr$^{-/-}$ mice with antagomir-21 reduced liver miR-21 expression not only as compared to Ldlr$^{-/-}$ mice treated with antagomir control and mice treated with PBS but also as compared to wild type mice.

The inventors also assessed whether miR-21 contributes to liver cell injury, inflammation and fibrosis in NASH. The inventors measured serum AST (aspartate aminotransferase) and ALT (alanine aminotransferase) concentrations, stained liver sections for the inflammatory cell markers CD68 (activated Kupffer cells) and CD3 (T cells) and analyzed liver expression of inflammatory (Tnfα and Mcp1) and fibrosis (Tgfβ and collagen-α2) genes and proteins. The inventors demonstrated that in the mouse model of NASH, serum AST and ALT levels, liver CD68 and CD3 staining, liver MCP1 and TNFα expression and Tgfβ and collagen-1α2 expression were higher in Ldlr$^{-/-}$ mice under high fat diet than in WT mice under chow diet.

The inventors surprisingly found that antagomir-21 reduced liver injury since it decreased both serum AST and ALT levels. Antagomir-21 also decreased the number of infiltrated T cells and reduced liver inflammation since it decreased inflammatory markers MCP1 and TNFα in the livers from Ldlr$^{-/-}$ mice under high fat diet as compared to control mice (Ldlr$^{-/-}$ mice under high fat diet treated with PBS or antagomir control). Antagomir-21 also decreased liver fibrosis since it decreased the 2 well-known fibrogenic-related genes in liver, Tgfβ and collagen-1α2.

The inventors demonstrated that the inhibition of miR-21 expression represents a suitable method for NASH treatment in patients.

Therapeutic Methods

Accordingly, the present invention relates to a miR-21 inhibitor compound for use in the treatment of NASH in a patient in need thereof.

As used herein, the term "miR-21" has its general meaning in the art and refers to the miR-21 sequence available from the data base http://microrna.sanger.ac.uk/sequences/under the miRBase Accession number MI0000077.

As used herein, the term "patient" denotes a mammal. In a preferred embodiment of the invention, a patient according to the invention refers to any patient (preferably human) afflicted with or susceptible to be afflicted with NASH.

As used herein, the term "NASH" has its general meaning in the art and refers to nonalcoholic steatohepatitis.

As used herein, the term "miR-21 inhibitor compound" refers to any nucleotidic compound able to prevent the action of miR-21. The miR-21 inhibitor compound of the present invention is a compound that inhibits or reduces the activity of miR-21. However, decreasing and/or reducing the activity of miR-21 can also be obtained by inhibiting miR-21 expression. The term "inhibiting miR-21 expression" means that the production of miR-21 in the liver or hepatocytes after treatment is less than the amount produced prior to treatment. One skilled in the art can readily determine whether miR-21 expression has been inhibited in a liver or hepatocytes, using for example the techniques for determining miRNA transcript level.

Suitable miR-21 inhibitor compounds include double-stranded RNA (such as short- or small-interfering RNA or "siRNA"), antagomirs, antisense nucleic acids, and enzymatic RNA molecules such as ribozymes. Each of these compounds can be targeted to a given miRNA and destroy or induce the destruction of the target miRNA. For example, expression of a given miRNA can be inhibited by inducing RNA interference of the miRNA with an isolated double-stranded RNA ("dsRNA") molecule which has at least 90%, for example 95%, 98%, 99% or 100%, sequence homology with at least a portion of the miRNA. In a preferred embodiment, the dsRNA molecule is a "short or small interfering RNA" or "siRNA".

siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence which is substantially identical to a nucleic acid sequence contained within the target miRNA.

As used herein, a nucleic acid sequence in a siRNA which is "substantially identical" to a target sequence contained within the target mRNA is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area. The siRNA can also be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA can also comprise a 3' overhang. As used herein, a "3" overhang" refers to at least one unpaired nucleotide extending from the 3'-end of a duplexed RNA strand. Thus, in one embodiment, the siRNA comprises at least one 3' overhang of 1 to about 6 nucleotides (which includes ribonucleotides or deoxyribonucleotides) in length, preferably from 1 to about 5 nucleotides in length, more preferably from 1 to about 4 nucleotides in length, and particularly preferably from about 2 to about 4 nucleotides in length. In a preferred embodiment, the 3' overhang is present on both strands of the siRNA, and is 2 nucleotides in length. For example, each strand of the siRNA can comprise 3' overhangs of dithymidylic acid ("TT") or diuridylic acid ("uu").

The siRNA can be produced chemically or biologically, or can be expressed from a recombinant plasmid or viral vector, as described above. Exemplary methods for producing and testing dsRNA or siRNA molecules are described in U.S. published patent application 2002/0173478 to Gewirtz and in U.S. published patent application 2004/0018176 to Reich et al., the entire disclosures of which are herein incorporated by reference.

Expression of a given miRNA can also be inhibited by an antisense nucleic acid. As used herein, an "antisense nucleic acid" refers to a nucleic acid molecule that binds to target RNA by means of RNA-RNA or RNA-DNA or RNA-peptide nucleic acid interactions, which alters the activity of the target RNA. Antisense nucleic acids suitable for use in the present methods are single-stranded nucleic acids (e.g., RNA, DNA, RNA-DNA chimeras, PNA) that generally comprise a nucleic acid sequence complementary to a contiguous nucleic acid sequence in a miRNA. Preferably, the antisense nucleic acid comprises a nucleic acid sequence that is 50-100% complementary, more preferably 75-100% complementary, and most preferably 95-100% complementary to a contiguous nucleic acid sequence in an miRNA. Nucleic acid sequences for the miRNAs are provided in Table A. Without wishing to be bound by any theory, it is believed that the antisense nucleic acids activate RNase H or some other cellular nuclease that digests the miRNA/antisense nucleic acid duplex.

In a preferred embodiment the inhibitor is an antagomir and/or an antisense oligonucleotide.

The term "antagomir" or "antagomiR-21" as used herein refers to a chemically engineered small RNA that is used to silence miR-21. The antagomir is complementary to the specific miRNA target with either mis-pairing or some sort of base modification. Antagomirs may also include some sort of modification to make them more resistant to degradation. In a preferred embodiment the antagomir is a chemically engineered cholesterol-conjugated single-stranded RNA analogue.

Inhibition of miRNAs can also be achieved with antisense 2'-O-methyl (2'-O-Me) oligoribonucleotides, 2'-O-methoxyethyl (2'-O-MOE), phosphorothioates, locked nucleic acid (LNA), morpholino oligomers or by use of lentivirally or adenovirally expressed antagomirs (Stenvang and Kauppinen (2008), Expert Opin. Biol. Ther. 8(1):59-81). Furthermore, MOE (2'-O-methoxyethyl phosphorothioate) or LNA (locked nucleic acid (LNA) phosphorothioate chemistry)-modification of single-stranded RNA analogous can be used to inhibit miRNA activity.

Antisense nucleic acids can also contain modifications of the nucleic acid backbone or of the sugar and base moieties (or their equivalent) to enhance target specificity, nuclease resistance, delivery or other properties related to efficacy of the molecule. Such modifications include cholesterol moieties, duplex intercalators such as acridine or the inclusion of one or more nuclease-resistant groups.

Antisense nucleic acids can be produced chemically or biologically, or can be expressed from a recombinant plasmid or viral vector, as described below. Exemplary methods for producing and testing are within the skill in the art; see, e.g., Stein and Cheng (1993), Science 261:1004 and U.S. Pat. No. 5,849,902 to Woolf et al., the entire disclosures of which are herein incorporated by reference.

Expression of a given miRNA can also be inhibited by an enzymatic nucleic acid. As used herein, an "enzymatic nucleic acid" refers to a nucleic acid comprising a substrate binding region that has complementarity to a contiguous nucleic acid sequence of a miRNA, and which is able to specifically cleave the miRNA. Preferably, the enzymatic nucleic acid substrate binding region is 50-100% complementary, more preferably 75-100% complementary, and most preferably 95-100% complementary to a contiguous nucleic acid sequence in a miRNA. The enzymatic nucleic acids can also comprise modifications at the base, sugar, and/or phosphate groups. An exemplary enzymatic nucleic acid for use in the present methods is a ribozyme.

The enzymatic nucleic acids can be produced chemically or biologically, or can be expressed from a recombinant plasmid or viral vector, as described below. Exemplary methods for producing and testing dsRNA or siRNA molecules are described in Werner and Uhlenbeck (1995), Nucl. Acids Res. 23:2092-96; Hammann et al. (1999), Antisense and Nucleic Acid Drug Dev. 9:25-31; and U.S. Pat. No. 4,987,071 to Cech et al, the entire disclosures of which are herein incorporated by reference.

The miR-21 inhibitor compound of the invention can be obtained using a number of standard techniques. For example the miR-21 inhibitor compound of the invention can be chemically synthesized or recombinantly produced using methods known in the art. Typically, miR-21 inhibitor compound of the invention are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

In some embodiments, of the invention, a synthetic miR-21 inhibitor compound of the invention contains one or more design elements. These design elements include, but are not limited to: (i) a replacement group for the phosphate or hydroxyl of the nucleotide at the 5' terminus of the complementary region; (ii) one or more sugar modifications. In certain embodiments, a synthetic miR-21 inhibitor compound of the invention has a nucleotide at its 5' end of the complementary region in which the phosphate and/or hydroxyl group has been replaced with another chemical group (referred to as the "replacement design"). In some cases, the phosphate group is replaced, while in others, the hydroxyl group has been replaced. In particular embodiments, the replacement group is biotin, an amine group, a lower alkylamine group, an acetyl group, 2'O-Me (2'oxygen-methyl), DMTO (4,4'-dimethoxytrityl with oxygen), fluorescein, a thiol, or acridine, though other replacement groups are well known to those of skill in the art and can be used as well. In particular embodiments, the sugar modification is a 2'O-Me modification. In further embodiments, there is one or more sugar modifications in the first or last 2 to 4 residues of the complementary region or the first or last 4 to 6 residues of the complementary region.

In a particular embodiment, the miR-21 inhibitor compound of the invention is resistant to degradation by nucleases. One skilled in the art can readily synthesize nucleic acids which are nuclease resistant, for example by incorporating one or more ribonucleotides that are modified at the 2'-position into the miRNAs. Suitable 2'-modified ribonucleotides include those modified at the 2'-position with fluoro, amino, alkyl, alkoxy, and O-allyl.

The present invention also relates to a vector comprising a miR-21 inhibitor compound according to the invention for use in the treatment of NASH.

Alternatively, the miR-21 inhibitor compound of the invention can be expressed from recombinant circular or linear DNA plasmids using any suitable promoter. Suitable promoters for expressing RNA from a plasmid include, e.g., the U6 or HI RNA pol III promoter sequences, or the cytomegalovirus promoters. Selection of other suitable promoters is within the skill in the art. The recombinant plasmids of the invention can also comprise inducible or regulatable promoters for expression of the miR-21 inhibitor compound of the invention in hepatocytes.

The miR-21 inhibitor compound of the invention that is expressed from recombinant plasmids can be isolated from cultured cell expression systems by standard techniques. The miR-21 inhibitor compound of the invention which is expressed from recombinant plasmids can also be delivered to, and expressed directly in, the hepatocytes. The use of recombinant plasmids to deliver the miR-21 inhibitor compound of the invention to hepatocytes is discussed in more detail below.

The miR-21 inhibitor compound of the invention can be expressed from a separate recombinant plasmid, or can be expressed from a unique recombinant plasmid. Preferably, the miR-21 inhibitor compound of the invention is expressed as the nucleic acid precursor molecules from a single plasmid, and the precursor molecules are processed into the functional miR-21 inhibitor compound by a suitable processing system, including processing systems extant within hepatocytes. Other suitable processing systems include, e.g., the in vitro *Drosophila* cell lysate system as described in U.S. published application 2002/0086356 to Tuschl et al. and the *E. coli* RNAse III system described in U.S. published patent application 2004/0014113 to Yang et al., the entire disclosures of which are herein incorporated by reference.

Selection of plasmids suitable for expressing the miR-21 inhibitor compound of the invention, methods for inserting nucleic acid sequences into the plasmid to express the gene products, and methods of delivering the recombinant plasmid to the cells of interest are within the skill in the art. See, for example, Zeng et al. (2002), Molecular Cell 9:1327-1333; Tuschl (2002), Nat. Biotechnol, 20:446-448; Brummelkamp et al. (2002), Science 296:550-553; Miyagishi et al. (2002), Nat. Biotechnol. 20:497-500; Paddison et al. (2002), Genes Dev. 16:948-958; Lee et al. (2002), Nat. Biotechnol. 20:500-505; and Paul et al. (2002), Nat. Biotechnol. 20:505-508, the entire disclosures of which are herein incorporated by reference.

In one embodiment, a plasmid expressing the miR-21 inhibitor compound of the invention comprises a sequence encoding a miR-21 inhibitor compound precursor under the control of the CMV intermediate early promoter. As used herein, "under the control" of a promoter means that the nucleic acid sequences are located 3' of the promoter, so that the promoter can initiate transcription of the miR-21 inhibitor compound coding sequences.

The miR-21 inhibitor compound of the invention can also be expressed from recombinant viral vectors. It is contemplated that the miR-21 inhibitor compound of the invention can be expressed from separate recombinant viral vectors, or from a unique viral vector. The miR-21 inhibitor compound expressed from the recombinant viral vectors can either be isolated from cultured cell expression systems by standard techniques, or can be expressed directly in hepatocytes. The use of recombinant viral vectors to deliver the miR-21 inhibitor compound to hepatocytes is discussed in more detail below.

The recombinant viral vectors of the invention comprise sequences encoding the miR-21 inhibitor compound of the invention and any suitable promoter for expressing the miR-21 inhibitor compound sequences. Suitable promoters include, for example, the U6 or HI RNA pol III promoter sequences, or the cytomegalovirus promoters. Selection of other suitable promoters is within the skill in the art. The recombinant viral vectors of the invention can also comprise inducible or regulatable promoters for expression of the miR-21 inhibitor compound in hepatocytes.

Any viral vector capable of accepting the coding sequences for the miR-21 inhibitor compound of the invention can be used; for example, vectors derived from adenovirus (AV); adenoassociated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate. For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes are within the skill in the art; see, e.g., Rabinowitz J. E. et al. (2002), J Virol 76:791801, the entire disclosure of which is herein incorporated by reference.

Selection of recombinant viral vectors suitable for use in the invention, methods for inserting nucleic acid sequences for expressing said miR-21 inhibitor compound of the invention into the vector, methods of delivering the viral vector to the cells of interest, and recovery of the expressed miR-21 inhibitor compound products are within the skill in the art. See, for example, Dornburg (1995), Gene Therap. 2:301-310; Eglitis (1988), Biotechniques 6:608-614; Miller (1990), Hum. Gene Therap. 1:5-14; and Anderson (1998), Nature 392:25-30, the entire disclosures of which are herein incorporated by reference.

Preferred viral vectors are those derived from AV and AAV. A suitable AV vector for expressing the miR-21 inhibitor compound of the invention, a method for constructing the recombinant AV vector, and a method for delivering the vector into target cells, are described in Xia et al. (2002), Nat. Biotech. 20:1006-1010, the entire disclosure of which is herein incorporated by reference. Suitable AAV vectors for expressing the miR-21 inhibitor compound of the invention, methods for constructing the recombinant AAV vector, and methods for delivering the vectors into target cells are described in Samulski et al. (1987), J. Virol. 61:3096-3101; Fisher et al. (1996), J. Virol., 70:520-532; Samulski et al. (1989), J. Virol. 63:3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference. Preferably, the miR-21 inhibitor compound of the invention is expressed from a single recombinant AAV vector comprising the CMV intermediate early promoter.

In one embodiment, a recombinant AAV viral vector of the invention comprises a nucleic acid sequence encoding a miR-21 inhibitor compound precursor in operable connection with a polyT termination sequence under the control of a human U6 RNA promoter. As used herein, "in operable connection with a polyT termination sequence" means that the nucleic acid sequences encoding the sense or antisense strands are immediately adjacent to the polyT termination signal in the 5' direction. During transcription of the miR-21 inhibitor compound sequences from the vector, the polyT termination signals act to terminate transcription.

The miR-21 inhibitor compound can be administered to a patient by any means suitable for delivering these compounds to liver or hepatocytes of the patient. For example, the miR-21 inhibitor compound can be administered by methods suitable to transfect cells of the patient with these compounds, or with nucleic acids comprising sequences encoding these compounds. Preferably, the cells are transfected with a plasmid or viral vector comprising sequences encoding at least one miR-21 inhibitor compound.

The miR-21 inhibitor compound can be administered to a patient by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., intra-retinal injection, or sub-retinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Preferred administration routes are injection, infusion and direct injection into the liver tissue.

In the present methods, a miR-21 inhibitor compound can be administered to the patient either as naked RNA, in combination with a delivery reagent, or as a nucleic acid (e.g., a recombinant plasmid or viral vector) comprising sequences that express the miR-21 inhibitor compound. Suitable delivery reagents include, e.g, the Minis Transit TKO lipophilic reagent; lipofectin; lipofectamine; cellfectin; polycations (e.g., polylysine), and liposomes.

Recombinant plasmids and viral vectors comprising sequences that express the miR-21 inhibitor compounds, and techniques for delivering such plasmids and vectors to hepatocytes, are discussed above.

In a preferred embodiment, liposomes are used to deliver a miR-21 inhibitor compound (or nucleic acids comprising sequences encoding them) to a patient. Liposomes can also increase the blood half-life of the gene products or nucleic acids. Liposomes suitable for use in the invention can be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream.

A variety of methods are known for preparing liposomes, for example, as described in Szoka et al. (1980), Ann. Rev. Biophys. Bioeng. 9:467; and U.S. Pat. Nos. 4,235,871, 4,501, 728, 4,837,028, and 5,019,369, the entire disclosures of which are herein incorporated by reference. The liposomes for use in the present methods can comprise a ligand molecule that targets the liposome to hepatocytes. Ligands which bind to receptors prevalent in hepatocytes, such as monoclonal antibodies that bind to hepatocytes antigens, are preferred. The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure. In a particularly preferred embodiment, a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is herein incorporated by reference. Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; animated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or derivatives thereof. Liposomes modified with PEG or PEG-derivatives are sometimes called "PEGylated liposomes".

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive animation using Na(CN)BH3 and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects will efficiently accumulate these liposomes; see Gabizon, et al. (1988), Proc. Natl. Acad. Sci., USA, 18:6949-53. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miR-21 inhibitor compounds (or nucleic acids comprising sequences encoding them) to hepatocytes.

One skilled in the art can readily determine a therapeutically effective amount of said compound to be administered to a given patient, by taking into account factors such as the size and weight of the patient; the extent of disease penetration; the age, health and sex of the patient; the route of administration; and whether the administration is regional or systemic. An effective amount of said compound can be based on the approximate or estimated body weight of a patient to be treated. Preferably, such effective amounts are administered parenterally or enterally, as described herein. For example, an effective amount of the compound is administered to a patient can range from about 5-10000 micrograms/kg of body weight, and is preferably between about 5-3000 micrograms/kg of body weight, and is preferably between about 700-1000 micrograms/kg of body weight, and is more preferably greater than about 1000 micrograms/kg of body weight. One skilled in the art can also readily determine an appropriate dosage regimen for the administration of the compound to a given patient. For example, the compound can be administered to the patient once (e.g., as a single injection or deposition).

Pharmaceutical Compositions

The miR-21 inhibitor compound of the invention may be used or prepared in a pharmaceutical composition.

In one embodiment, the invention relates to a pharmaceutical composition comprising a miR-21 inhibitor compound and a pharmaceutical acceptable carrier for use in the treatment of NASH in a patient in need thereof.

The miR-21 inhibitor compounds of the invention are preferably formulated as pharmaceutical compositions, prior to administering to a patient, according to techniques known in the art. Pharmaceutical compositions of the present invention are characterized as being at least sterile and pyrogen-free. As used herein, "pharmaceutical formulations" include formulations for human and veterinary use. Methods for preparing pharmaceutical compositions of the invention are within the skill in the art, for example as described in Remington's Pharmaceutical Science, 17th ed., Mack Publishing Company, Easton, Pa. (1985), the entire disclosure of which is herein incorporated by reference.

The present pharmaceutical formulations comprise miR-21 inhibitor compound (e.g., 0.1 to 90% by weight), or a physiologically acceptable salt thereof, mixed with a pharmaceutically-acceptable carrier. The pharmaceutical formulations of the invention can also comprise miR-21 inhibitor compound which are encapsulated by liposomes and a pharmaceutically-acceptable carrier. Preferred pharmaceutically-acceptable carriers are water, buffered water, normal saline, 0.4% saline, 0.3% glycine, hyaluronic acid and the like.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include, e.g., physiologically biocompatible buffers (e.g., tromethamine hydrochloride), additions of chelants (such as, for example, DTPA or DTPA-bisamide) or calcium chelate complexes (such as, for example, calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically acceptable carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of the miR-inhibitor compound. A pharmaceutical composition for aerosol (inhalational) administration can comprise 0.01-20% by weight, preferably 1%-10% by weight, of the miR-21 inhibitor compound encapsulated in a liposome as described above, and a propellant. A carrier can also be included as desired; e.g., lecithin for intranasal delivery.

Pharmaceutical compositions of the invention may include any further agent which is used in the prevention or treatment of NASH. For example, the anti-NASH may include antifibrotic agents, anti-inflammatory agents, insulins sensitizers such as thiazolidinediones (TZDs), metformin and biguanides, lipid-lowering agents such as statins and fibrates, antioxidants such as vitamin E, hepatoprotective agents such as ursodeoxycholic acid (UDCA), and other agents, suppressing renin-angiotensin system (RAS) system, probiotics and polyunsatured fatty acids (PUFAs).

In one embodiment, said additional active agents may be contained in the same composition or administrated separately.

In another embodiment, the pharmaceutical composition of the invention relates to combined preparation for simultaneous, separate or sequential use in the treatment of NASH.

The invention will be further illustrated by the following figures and examples. However, these examples and figures should not be interpreted in any way as limiting the scope of the present invention.

FIGURES

FIG. 1: miR-21 in overexpressed in the liver of NASH patients (A) and of Ldlr$^{-/-}$ mice under high fat diet (B). A. miR-21 expression normalized to U6 snRNA in the liver of NASH patients and of individuals with histologically normal liver (controls). B. miR-21 expression normalized to U6 snRNA in the liver of wild type (WT) mice under chow diet and in Ldlr$^{-/-}$ mice under high fat diet treated with the vehicle (PBS), antagomir control or antagomir-21. *, p<0.05 vs. Ldlr$^{-/-}$ mice treated with PBS; **, p<0.01 vs. Ldlr$^{-/-}$ mice treated with PBS; #, p<0.05 vs. Ldlr$^{-/-}$ mice treated with antagomir control; ##, p<0.01 vs. Ldlr$^{-/-}$ mice treated with antagomir control; §§, p<0.01 vs. wild type mice. Data are given as median (horizontal bar) and interquartile range (error bar).

Figure 2:
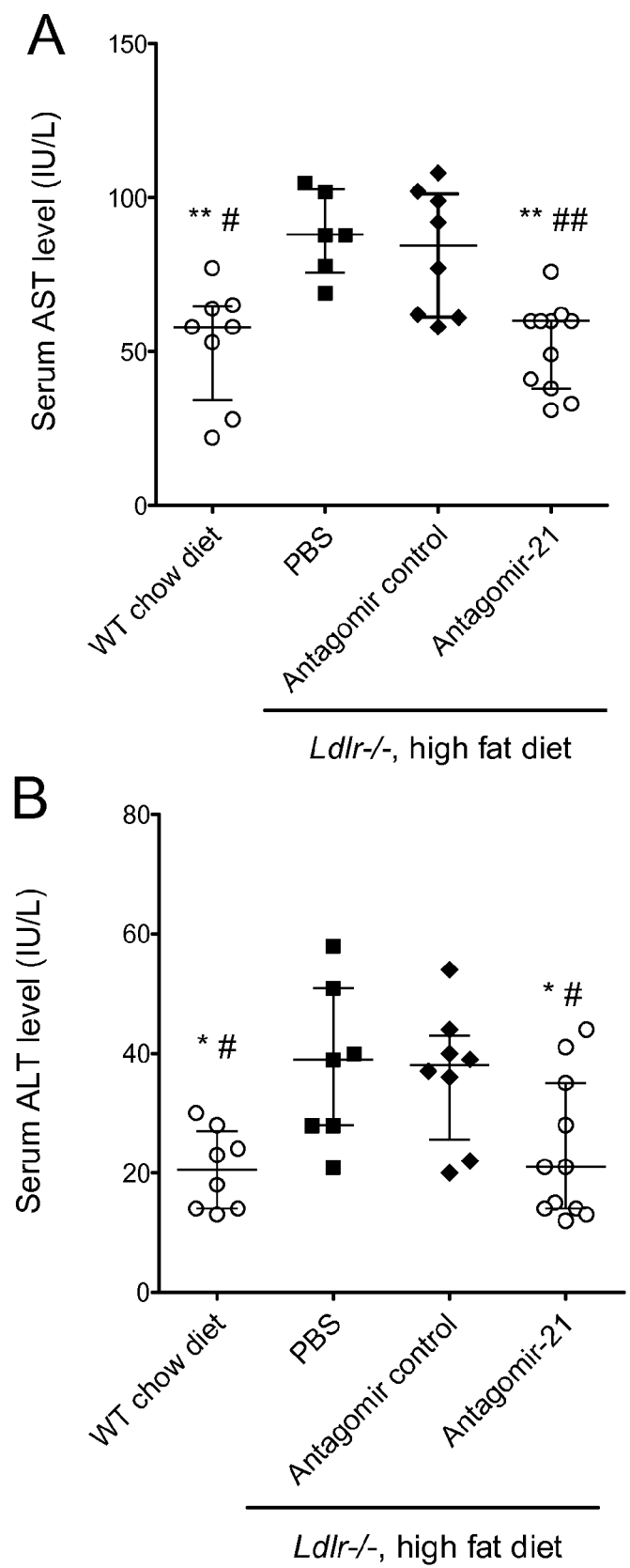
Figure 2:
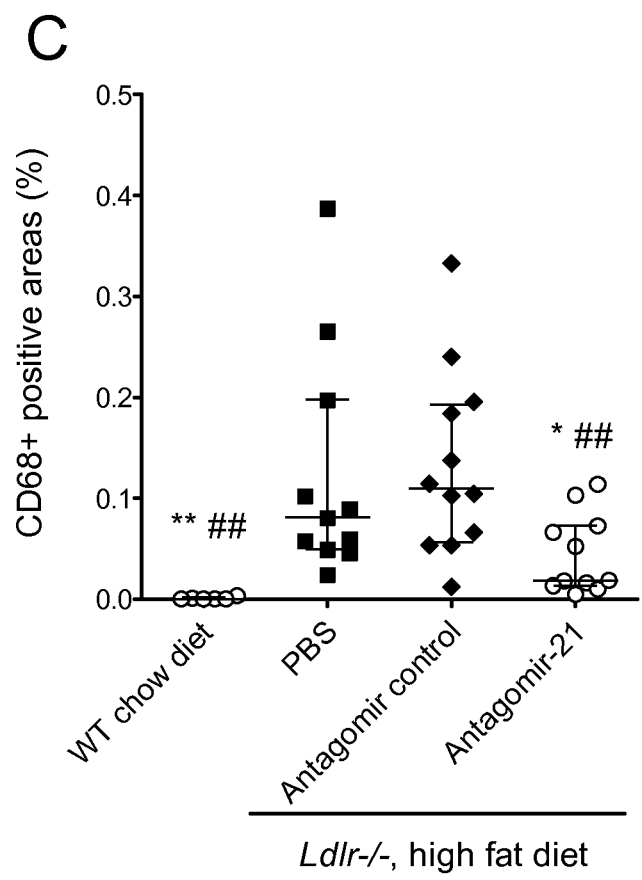
Figure 2:
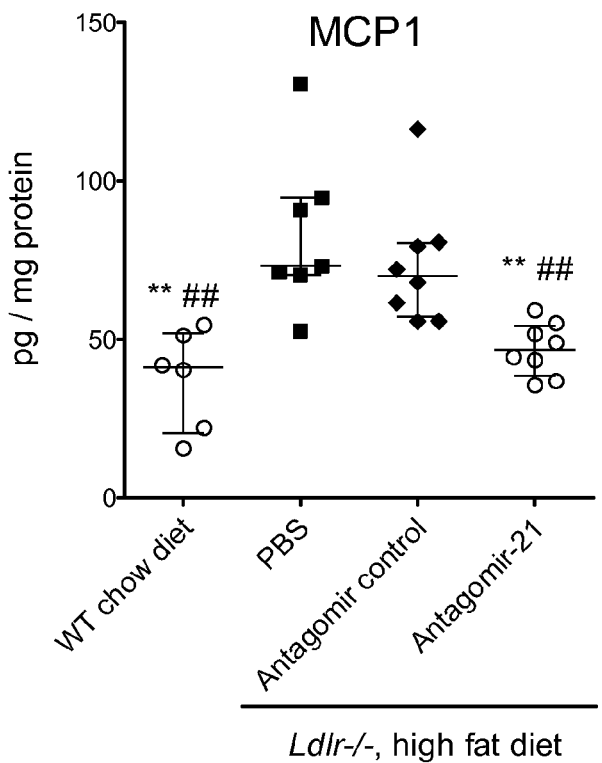
Figure 2:
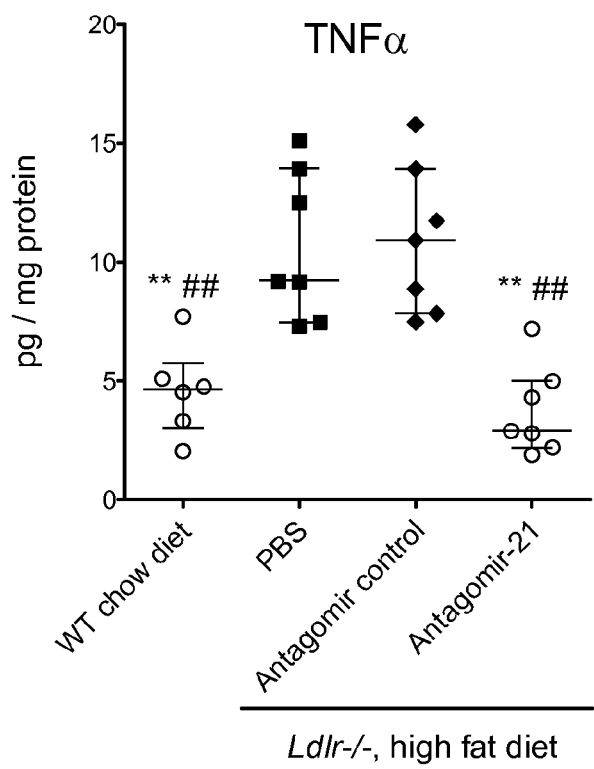

FIG. 2: Antagomir-21 reduces liver injury and liver inflammation. Antagomir-21 reduces serum AST (A) and ALT (B) levels, as well as CD68+ cells infiltrates (C, quantification) and MCP1 (D) and TNFα (E) liver protein levels.
*, p<0.05 vs. Ldlr$^{-/-}$ mice treated with PBS; **, p<0.01 vs. Ldlr$^{-/-}$ mice treated with PBS; #, p<0.05 vs. Ldlr$^{-/-}$ mice treated with antagomir control; ##, p<0.01 vs. Ldlr$^{-/-}$ mice treated with antagomir control.
Data are given as median (horizontal bar) and interquartile range (error bar).
Samples were randomly selected in each group of mice.

Figure 3:
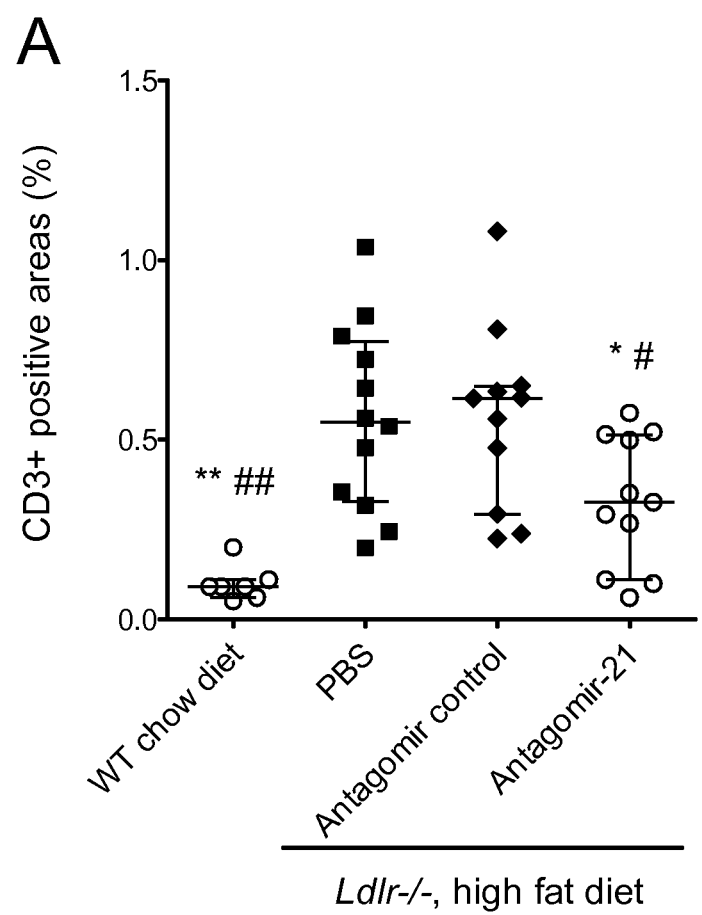
Figure 3:
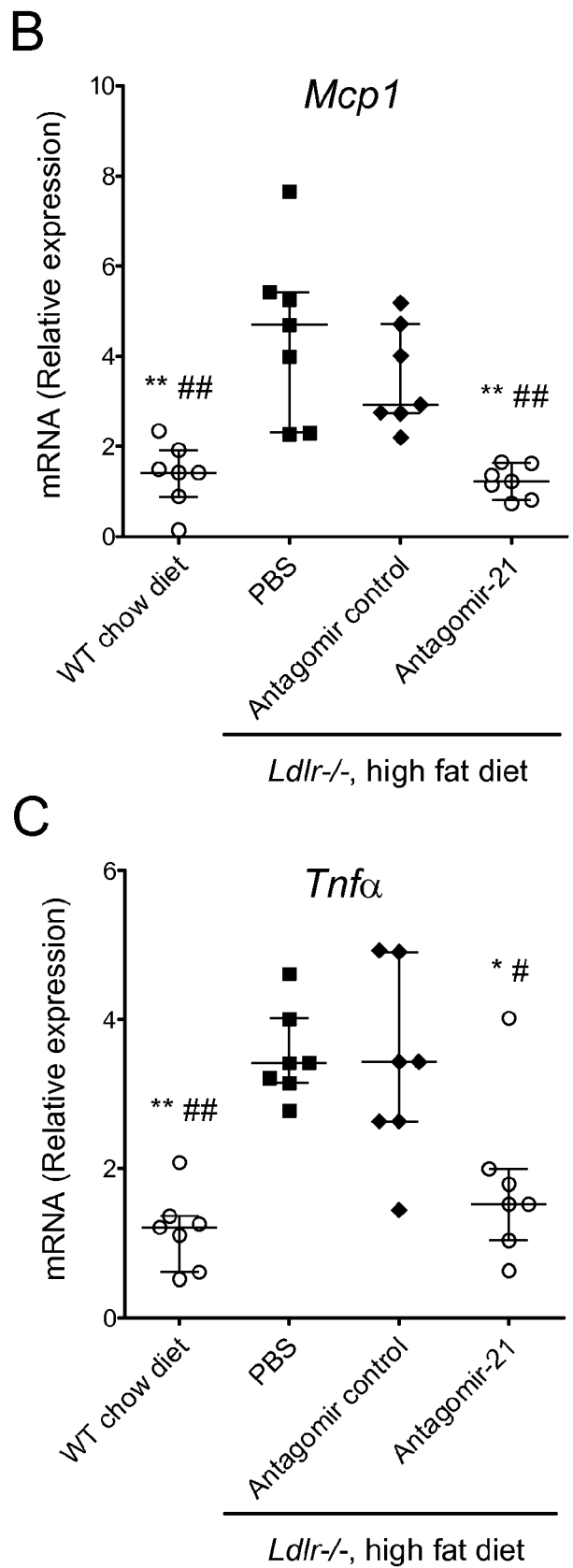

FIG. 3: Antagomir 21 reduces liver inflammation.
Antagomir 21 reduces liver CD3+ cells infiltrates (A, quantification) as well as liver Gapdh normalized Mcp1 (B), and Tnfα (C) mRNA expression.
*, p<0.05 vs. Ldlr$^{-/-}$ mice treated with PBS; **, p<0.01 vs. Ldlr$^{-/-}$ mice treated with PBS; #, p<0.05 vs. Ldlr$^{-/-}$ mice treated with antagomir control; ##, p<0.01 vs. Ldlr$^{-/-}$ mice treated with antagomir control.
Data are given as median (horizontal bar) and interquartile range (error bar).

Figure 4:
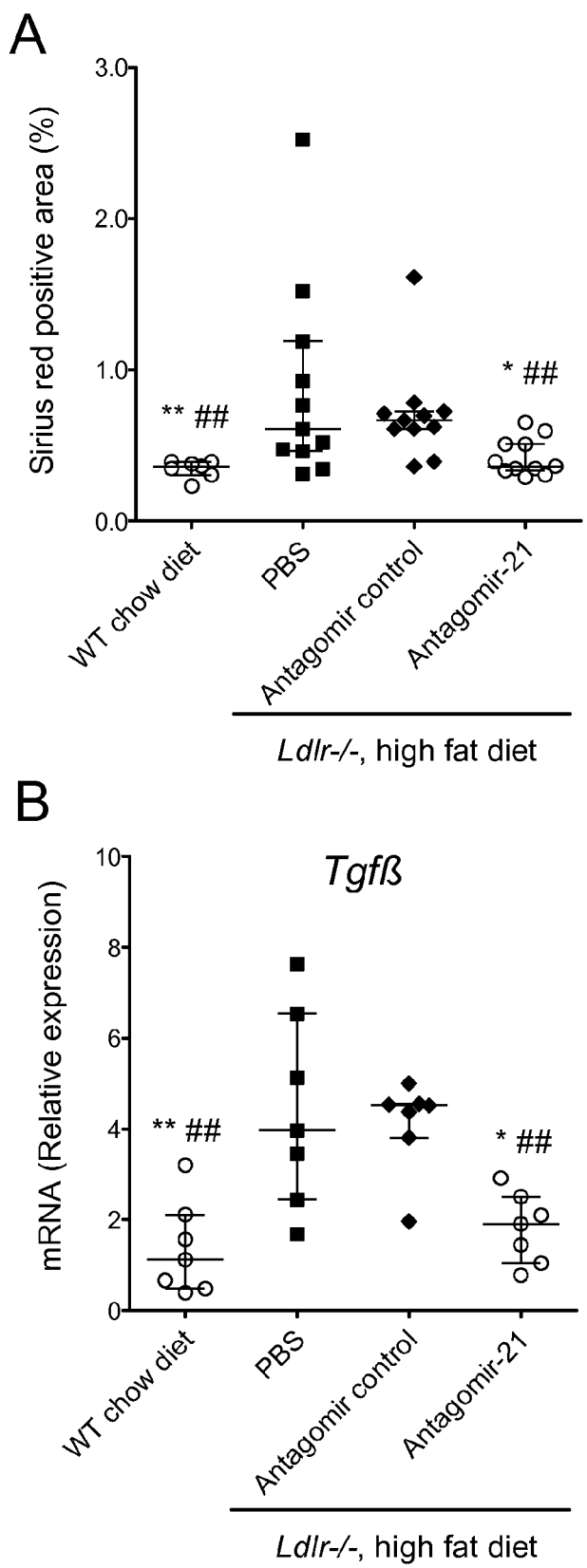
Figure 4:
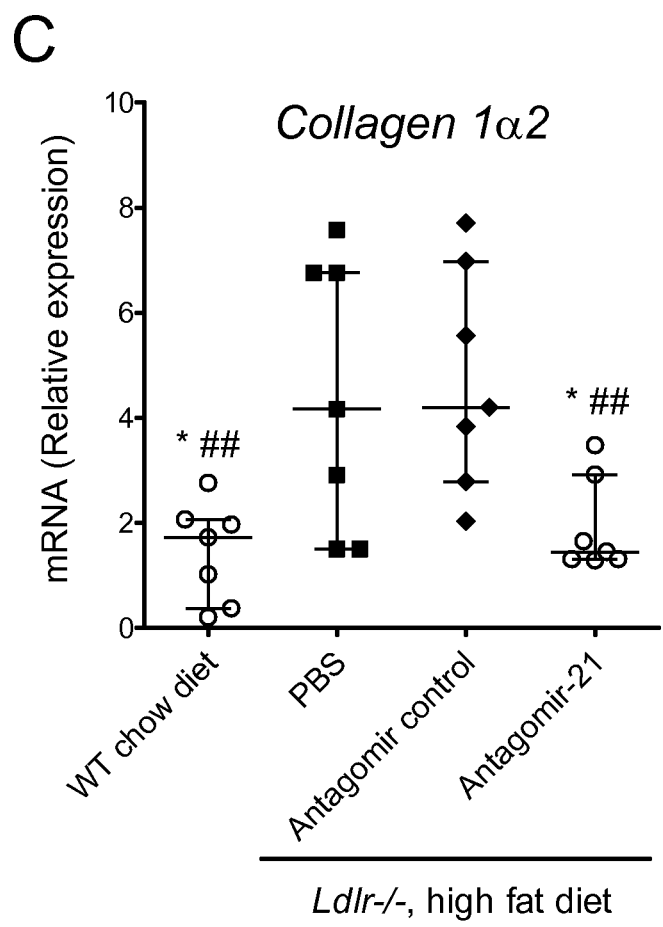

FIG. 4: Antagomir-21 reduces liver fibrosis and expression of fibrogenic-related genes. Antagomir-21 reduces liver collagen staining (Sirius Red; A, quantification), as well as liver Gapdh-normalized Tgfβ (B), and collagen-1α2 (C) mRNA expression.
*, p<0.05 vs. Ldlr$^{-/-}$ mice treated with PBS; **, p<0.01 vs. Ldlr$^{-/-}$ mice treated with PBS; #, p<0.05 vs. Ldlr$^{-/-}$ mice treated with antagomir control; ##, p<0.01 vs. Ldlr$^{-/-}$ mice treated with antagomir control.
Data are given as median (horizontal bar) and interquartile range (error bar).
Samples were randomly selected in each group of mice.

Figure 5:
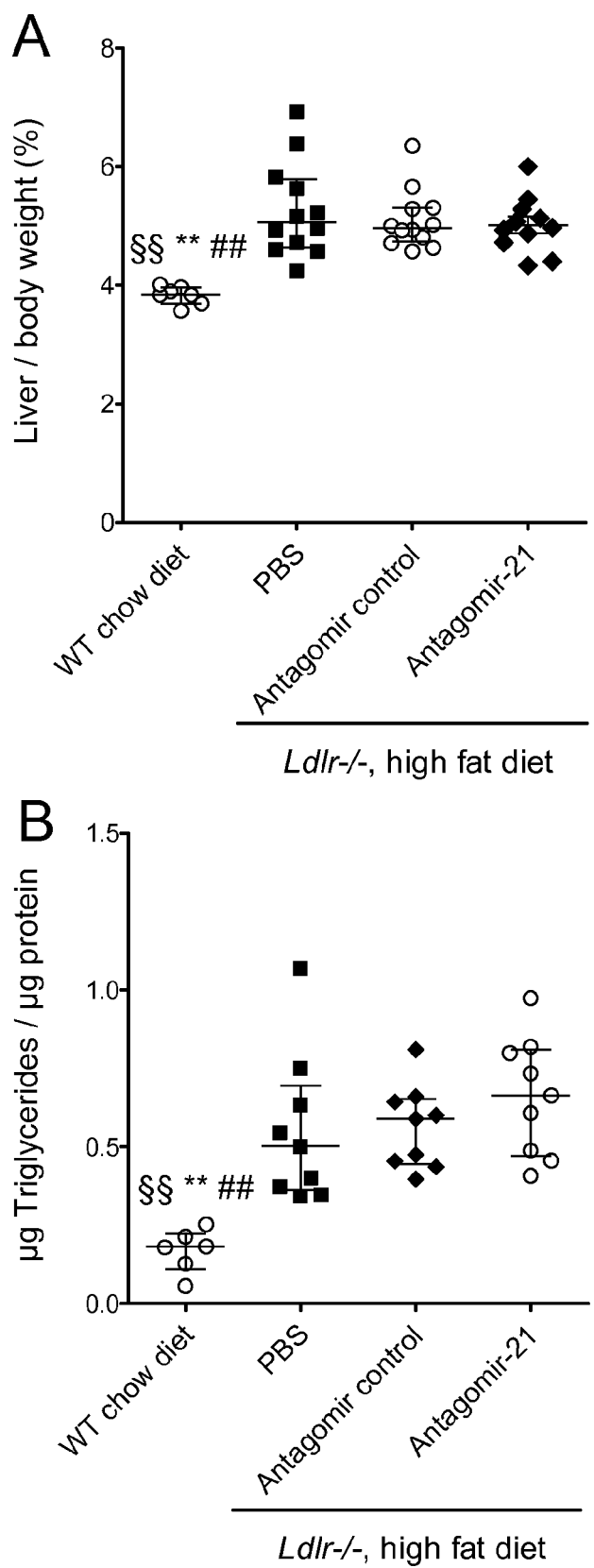
Figure 5:
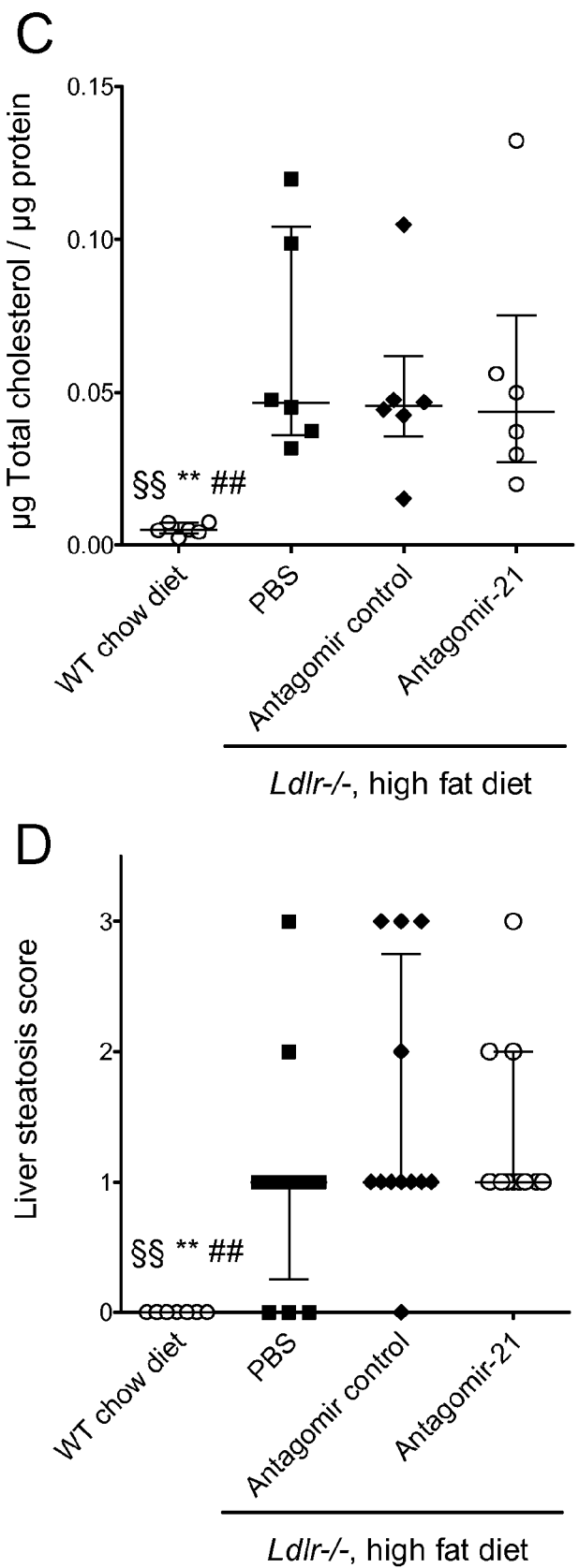

FIG. 5: Antagomir-21 does not change liver lipid accumulation. A. Liver weight expressed as a percentage of total body weight. B and C. Liver triglycerides and total cholesterol levels. D. Quantification of liver steatosis by hematoxylin and eosin staining. The amount of steatosis, defined as the percentage of hepatocytes with fat droplets, was scored using the following scale: 0 (<5%), 1 (5-33%), 2 (34-66%) and 3 (>67%).
**, p<0.01 vs. Ldlr$^{-/-}$ mice treated with PBS; ##, p<0.01 vs. Ldlr$^{-/-}$ mice treated with antagomir control; §§, p<0.01 vs. Ldlr$^{-/-}$ mice treated with antagomir-21. There was no difference between all 3 groups of Ldlr$^{-/-}$ mice in any of these parameters.
Data are given as median (horizontal bar) and interquartile range (error bar).

EXAMPLE

Methods

Patients

Ten patients who underwent liver resection between February and June 2012 were included. Five had NASH defined using the SAF score {Bedossa, 2012 #76} and 5 had no or mild abnormalities at liver histological examination. All patients gave informed consent. Patients' features are presented in Table 1.

Animals

All mice were on a C57BL/6 background. Eight-week-old male Ldl receptor-deficient (Ldlr$^{-/-}$) (Charles River, L'isle d'Abresle, France) mice were put on a high fat diet containing 1.25% cholesterol and 15% cacao butter (Safe Diets) for 14 weeks. When 12 and 17 week old, mice received a retroorbital intravenous injection of antagomir-21 (sequence 5'-UCAACAUCAGUCUGAUAAGCUA-3'; 16 mg/kg body weight, VBC Biotech, Vienna, Austria), or of antagomir control (sequence 5'-AAGGCAAGCUGACCCUGAAGUU-3'; 16 mg/kg body weight; VBC Biotech Vienna, Austria) or of phosphate buffer saline (PBS). All mice groups were euthanized at the age of 22 weeks. All experiments were performed in accordance with the guidelines formulated by the European Community for experimental animal use (L358-86/609EEC) and were approved by the French Ministry of Agriculture (agreement n° A75-15-32). C57BL/6 wild type untreated mice of the same age were used as control.

Blood was collected from the orbital sinus 2 days before sacrifice after an overnight fast period and processed to obtain serum (one centrifugation at 10,000 g for 10 min at room temperature). On the day of sacrifice, mice were sedated with 2.5% isofluorane and blood was collected from the inferior vena cava into a 25 gauge×1' needle pre-coated with 3.8% sodium citrate. Blood was spun at 1,500×g for 15 minutes to prepare platelet poor plasma and stored at −80° C. The mice were then humanely euthanized. Livers were isolated and snap frozen in liquid nitrogen and stored at −80° C. or fixed in formalin and paraffin-embedded.

RNA Isolation and microRNA Quantification

Total RNA was extracted from snap frozen human or mouse liver samples with Trizol reagent according to the manufacturer's instructions (Invitrogen, Paris, France). MiR-21 level was quantified using Taqman assay (Tm 00397, Applied Biosystems) following the manufacturer's instructions. U6 snRNA (Tm 001973, Applied Biosystems) was used as endogenous control.

In Situ Hybridization

In situ hybridization was adapted from a previously described method {Bonauer, 2009 #101}. Briefly, 3 μm-thick paraffin embedded liver sections were post-fixed in 4% paraformaldehyde for 10 min, and then acetylated for 10 min. After washes with PBS, sections were incubated with protein kinase K (Sigma-Aldrich) at 37° C. for 5 min. After washes with PBS, sections were incubated with hybridization buffer for 5 hours at room temperature. MiRNA probes [miR-21, 5'-3'-Digoxigenin (DIG)-labeled LNA probe, 20 nmol/L; U6snRNA, 3'-DIG labeled LNA probe, 10 nmol/L, Exiqon] were mixed with 150 μL denaturation buffer and then incubated with the sections overnight at 56° C. Then, the sections were washed with decreasing concentrations of saline-sodium citrate (SSC) buffer (Invitrogen) (5 min at 56° C. once in 5×SSC buffer, then twice in 1×SSC buffer, then 3 times in 0.2×SSC buffer) and then washed in PBS. After incubation for 1 hour in a blocking solution (Tris+3% fetal calf serum+ 0.1% Tween-20), sections were incubated with an anti-DIG antibody conjugated with alkaline phosphatase (Roche; 1:2000) overnight at 4° C. Sections were then incubated with NBT/BCIP (Promega) in NTMT buffer with levamisole (0.2 mmol/L; Sigma-Aldrich) for 48 hours in the dark at room temperature. NBT/BCIP solution was changed every 12 hours. Afterwards, slides were fixed in 4% paraformaldehyde for 10 min and mounted with Fluoprep (Biomerieux).

Metabolic Analyses

Serum alanine aminotransferase (ALT) and aspartate aminotransferase (AST) activities, and fasting glucose, total cholesterol, HDL, and triglyceride levels were determined using commercial enzymatic kits on a DxC800 analyzer (Beckman-Coulter, Villepinte, France).

Blood Pressure Measurement

Blood arterial pressure was measured every 30 seconds at the tail of conscious mice using CODA non invasive blood pressure device (Kent Scientific Corporation) (mean value of 8 measures).

Histology

Paraffin-embedded liver sections (3 µm-thick) were stained with hematoxylin-eosin (HE; Hematoxilin, RAL diagnostics; and Eosin, RAL diagnostics), Picro-sirius (Sirius red, RAL diagnostics; picric acid, VWR Prolabo), rabbit anti-CD3 antibody (DAKO, #A0452) and a monoclonal rat anti-mouse CD68 antibody (AbD Serotec). Steatosis was defined as the percentage of hepatocytes containing large or medium-sized lipid droplets. Steatosis was scored on hematoxylin-eosin stained sections by a single experienced pathologist (VP) who was blinded to the clinical and laboratory data. The following scale was used: 0 (<5%), 1 (5-33%), 2 (34-66%) and 3 (>67%). The Sirius red positive area was measured in at least ten fields without vessels or capsule (magnification ×200) and quantified using ImageJ software. Immune cells (CD3+ or CD68+) were counted in 15 or more microscope views (original magnification, ×200) and were noted as the percentage of positive area.

Frozen liver sections (4 µm) were stained with the neutral lipid marker Oil Red 0 (Sigma-Aldrich) to confirm steatosis.

Real-Time Quantitative Polymerase Chain Reaction cDNA synthesis was performed with QuantiTect Reverse Transcription Kit (Qiagen). Polymerase chain reaction was performed on an ABI StepOne Plus with the use of Power SYBR Green PCR Master Mix (Applied Biosystems). Mouse Gapdh was used to normalize sample amplification. $2^{Ct}$ calculation was used to determine relative gene expression.

Hepatic Lipid Analysis 50 mg of frozen liver tissue was homogenized by sonication in 1 mL of acetone. After overnight incubation at 4° C., samples were centrifuged at 4,000 g for 10 minutes. Triglyceride (Diasys, Holzheim, Germany) and total cholesterol (Biomérieux, Craponne, France) contents were then measured in the supernatant using enzymatic kits according to manufacturers instructions. Triglycerides and total cholesterol content were normalized to protein content determined by Dc Protein Assay (BioRad, Marnes la Coquette, France).

Liver Cytokine and Chemokine Protein Level

Cytokines were quantified on total liver protein extract. For this, frozen liver tissue samples were homogenized in THE buffer (1% Nonidet P40, 10 mmol/L Tris-Hcl [pH 7.5], 150 mmol/L NaCl, 1 mmol/L ethylene diamine tetraacetic acid) containing a cocktail of protease and phosphatase inhibitors (Roche). The suspension was centrifuged at 20,000 g for 20 minutes at 4° C. The supernatant was then stored at −80° C. before use. Levels of tumor necrosis factor (TNF)-α and monocyte chemoattractant protein-1 (MCP-1) in the liver extracts were measured using a cytometric bead array (Mouse Flowcytomix, eBiosciences). Cytokines levels were normalized to protein content determined by Dc Protein Assay (Bio-Rad, Marnes-la-Coquette, France).

PPAR Expression Analysis

Liver proteins were prepared in RIPA buffer (50 mmol/L Tris-HCL [pH 7.4], 1 mmol/L EDTA, 150 mmol/L NaCl, 20 mmol/L glycerophosphate, 0.1% SDS, 0.1% deoxycholate, 1% Triton, complete protease inhibitor cocktail tablet [Roche]). Membranes were incubated with anti-PPAR alpha (Abcam). After secondary antibody incubation (Amersham), immunodetection proceeded using an enhanced chemiluminescence kit (ECL Plus, Amersham), and bands were revealed using the Las1000 imaging system and Image Gauge software (Fuji). After initial immunodetection, all membranes were stripped of antibodies and reprobed with an anti-GAPDH antibody (Millipore).

Statistics

Quantitative variables were expressed as median (interquartile range). Comparisons between groups of independent quantitative variables were performed using Mann-Whitney test. All tests were two-sided and used a significance level of 0.05. Data analysis was performed with SPSS 17.0 (SPSS Inc., Chicago, Ill.).

Results

Expression of miR-21 is Increased in Biliary and Inflammatory Cells in the Liver of NASH Patients and of Ldlr$^{-/-}$ Mice Under High Fat Diet The inventors first determined by real-time PCR miR-21 expression in the liver of NASH patients as compared to controls with no or mild abnormalities at liver histological examination. As shown in FIG. 1A, miR-21 was overexpressed in the liver of NASH patients. We then assessed miR-21 expression in Ldlr$^{-/-}$ mice fed a high fat diet. This mouse model of NASH reproduced human features since miR-21 was upregulated in the liver in these mice (FIG. 1B). Using in situ hybridization, we observed that miR-21 was primarily expressed in biliary and inflammatory cells in the liver of NASH patient (data not shown) and of Ldlr$^{-/-}$ mice under high fat diet (data not shown). In accordance with real-time PCR results, the staining frequency and intensity of miR-21 was higher in NASH patients and in Ldlr$^{-/-}$ mice under high fat diet than in controls. In these controls, miR-21 staining was restricted to biliary cells and was mild.

In order to determine the potential role of miR-21 in NASH, the inventors used an antagomir strategy. As shown in FIG. 1B, antagomir-21 strongly decreased liver miR-21 expression in Ldlr$^{-/-}$ mice under high fat diet. As shown in Table 2, antagomir-21 had no effect on serum fasting glucose, total cholesterol, HDL, and triglyceride levels. Antagomir-21 did not affect arterial blood pressure either. These results thus establish the use of antagomir-21 in Ldlr$^{-/-}$ mice under high fat diet as a valid strategy to investigate the role miR-21 in NASH.

Antagomir-21 Reduces Liver Injury and Liver Inflammation.

To determine whether miR-21 contributes to liver cell injury and inflammation in NASH, the inventors measured serum aminostranferase levels, stained liver sections for the inflammatory cell markers CD68 (activated Kupffer cells) and CD3 (T cells) and analyzed liver MCP1 and TNFα mRNA and protein levels (FIG. 2 and FIG. 3). As expected in this mouse model of NASH, serum AST and ALT levels, liver CD68 and CD3 staining and liver MCP1 and TNFα expression were higher in Ldlr$^{-/-}$ mice under high fat diet than in WT mice under chow diet.

Antagomir-21 reduced liver cell injury since it decreased both serum AST and ALT levels (FIGS. 2A and B). Scoring of the CD68 positive sections revealed a reduction in size of foamy Kupffer cells in Ldlr$^{-/-}$ mice under high fat diet treated with antagomir-21 (FIGS. 2C and D). As shown in FIGS. 3A and B, antagomir-21 also decreased the number of infiltrated T cells. Further confirming the reduced hepatic inflammation resulting from antagomir-21 treatment, both gene and protein expression analysis showed a significant decrease in the inflammatory markers MCP1 and TNFα in the livers from Ldlr$^{-/-}$ mice under high fat diet treated with antagomir-21 as compared to control mice (Ldlr$^{-/-}$ mice under high fat diet treated with PBS or antagomir control) (FIGS. 2 D and E and FIGS. 3 B and C).

Antagomir-21 Reduces Liver Fibrosis.

Hepatic fibrosis is viewed as one of the advanced consequences of NASH. After 14 weeks of high fat diet, Ldlr$^{-/-}$ mice had more liver fibrosis than WT mice under chow diet as evidenced by collagen staining with Sirius red (FIG. 4A). Antagomir-21 strongly reduced liver fibrosis (FIG. 4A). Gene expression of 2 well-known fibrogenic-related genes in liver, Tgfβ and collagen-1α2, confirmed the findings of the Sirius red staining (FIGS. 4B and C).

Antagomir-21 does not Change Liver Lipid Accumulation.

After 14 weeks high fat diet, Ldlr$^{-/-}$ mice had a clear increase steatosis compared with WT mice on a chow diet, as attested by liver weight to total body weight ratio, liver triglycerides and total cholesterol levels and hematoxylin and eosin staining (FIG. 5). As shown in FIG. 5, all these techniques concurred for showing that antagomir-21 did not change liver lipid level.

CONCLUSION

The results demonstrate in vivo that miR21 plays a crucial role in NASH and that inhibiting mir-21 represents a suitable method for NASH treatment.

TABLE 1

Patients' Main Features.

| | Controls with no or mild abnormalities at liver histological examination (n = 5) | NASH patients (n = 5) |
|---|---|---|
| Sex | 3 women, 2 men | 1 woman, 4 men |
| Age (years) | 71 (55-79) | 69 (64-72) |
| Indication for liver surgery | Colon or rectum cancer metastasis (n = 5) | Liver transplantation for decompensated cirrhosis (n = 1) Hepatocellular carcinoma (n = 2) Colon cancer metastasis (n = 1) Cholangiocarcinoma (n = 1) |
| Steatosis: S0, S1, S2, S3 | 4, 1, 0, 0 | 0, 3, 1, 1 |
| Ballooning: 0, 1, 2 | 5, 0, 0 | 0, 2, 3 |
| Lobular inflammation: 0, 1, 2 | 2, 3, 0 | 0, 5, 0 |
| Fibrosis: F0, F1, F2, F3, F4 | 0, 4, 1, 0, 0 | 0, 1, 1, 1, 2 |

Data are median (interquartile range) or frequency (%).

The steatosis score assessed the quantities of large or medium-sized lipid droplets, but not foamy microvesicules, from 0 to 3: S0: <5%; S1: 5-33%; S2: 34-66%; S3: >67%.

Ballooning was graded from 0 to 2: 0, normal hepatocytes with cuboidal shape and pink eosinophilic cytoplasm; 1, presence of clusters of hepatocytes with a rounded shape and pale cytoplasm usually reticulated; 2, same as grade 1 with some enlarged hepatocytes, at least 2 fold that normal cells. {Bedossa, 2012 #45}

Lobular inflammation was defined as a focus of 2 or more inflammatory cells within the lobule. Foci were counted at 20× magnification: 0, none; 1, ≤2 foci per 20×; 2, >2 foci per 20× field.

Stage of fibrosis was assessed using the score described by NASH-CRN as follows: stage 0 (F0), none; stage 1 (F1), perisinusoidal zone 3 or portal fibrosis; stage 2 (F2), perisinusoidal and periportal fibrosis without bridging; stage 3 (F3), bridging fibrosis; and stage 4 (F4), cirrhosis. {Kleiner, 2005 #44}

Abbreviations: NASH, non alcoholic steatohepatitis

TABLE 2

Metabolic parameters.

| | WT mice | Ldlr$^{-/-}$ mice treated with | | |
|---|---|---|---|---|
| | chow diet (n = 7) | PBS (n = 11 to 12) | Antagomir control (n = 10 to 12) | Antagomir-21 (n = 10 to 11) |
| Fasting serum glucose (mmol/L) | NA | 5.5 (4.1-8.9) | 5.5 (4.5-9.0) | 6.1 (3.7-8.9) |
| Serum triglyceride (mmol/L) | 0.7 (0.6-1.0) | 4.2 (2.3-5.2) | 3.8 (2.6-4.2) | 3.2 (2.9-3.3) |
| Serum total cholesterol (mmol/L) | 1.9 (1.7-2.0) | 39.8 (33.7-45.4) | 34.5 (31.4-37.2) | 31.7 (30.2-35.2) |
| Serum HDL cholesterol (mmol/L) | 1.2 (1.1-1.3) | 5.9 (5.4-6.3) | 5.8 (4.9-6.4) | 5.2 (4.2-6.1) |
| Mean arterial pressure (mm Hg) | NA | NA | 102 (83-113) | 98 (79-112) |

Data are median (interquartile range).
WT mice fed with chow diet had significantly lower serum triglyceride, total and HDL cholesterol than Ldlr$^{-/-}$ mice treated with PBS, or antagomir control, or antagomir-21 (p<0.001 for each comparison).

There was no significant difference between Ldlr$^{-/-}$ mice treated with antagomir control and antagomir-21 and between Ldlr$^{-/-}$ mice treated with antagomir control and PBS in any of these parameters. Antagomir-21 reduced serum total cholesterol as compared with PBS (p=0.003) but did not change other variables.

Abbreviations: NA, not available; WT, wild type.

REFERENCES

Throughout this application, various references describe the state of the art to which this invention pertains. The disclosures of these references are hereby incorporated by reference into the present disclosure.

The invention claimed is:

1. A method for reducing liver inflammation in a subject having liver inflammation comprising the step of administering to said subject a therapeutic amount of a chemically modified miR-21 inhibitor and a pharmaceutically acceptable carrier, wherein said step of administering reduces said liver inflammation in said subject.

2. The method of claim 1, wherein said subject suffers from NASH.

3. The method of claim 1, wherein said chemically modified miR-21 inhibitor is selected from the group consisting of double-stranded RNA, antagomirs, antisense nucleic acids, and enzymatic RNA molecules.

4. The method of claim 1, wherein said chemically modified miR-21 inhibitor is encoded by a vector.

5. The method of claim 3, wherein said chemically modified miR-21 inhibitor is an enzymatic RNA molecule.

* * * * *